United States Patent [19]

Nakashima et al.

[11] Patent Number: 4,730,052
[45] Date of Patent: Mar. 8, 1988

[54] METHOD FOR PREPARING UNSYMMETRICAL 1,4-DIHYDROPYRIDINE-3,5-DICARBOXYLIC ACID DIESTERS

[75] Inventors: Yoshimoto Nakashima; Toshihisa Ogawa, both of Ageo; Atsuro Nakazato; Yukinari Kumazawa, both of Ohmiya; Kaoru Sota, Tokorozawa, all of Japan

[73] Assignee: Taisho Pharmaceutical Co., Ltd., Tokyo, Japan

[21] Appl. No.: 753,162

[22] Filed: Jul. 9, 1985

[30] Foreign Application Priority Data

Jul. 13, 1984 [JP] Japan ................... 59-145597
Jul. 13, 1984 [JP] Japan ................... 59-145598
Jul. 13, 1984 [JP] Japan ................... 59-145599

[51] Int. Cl.⁴ .......................................... C07D 211/90
[52] U.S. Cl. ................................................. 546/321
[58] Field of Search ..................................... 546/321

[56] References Cited

U.S. PATENT DOCUMENTS 3,996,234 12/1976 Bossert et al. ................ 546/321
4,483,985 11/1984 Wehinger et al. .............. 546/321

FOREIGN PATENT DOCUMENTS 898024 4/1984 Belgium .
0092936 4/1983 European Pat. Off. .

OTHER PUBLICATIONS

Bald, E. "The Synthetic Utility of 2-Halopyridinium Salts" Chemica Scripta 1979, 13 (1) p. 47.
Karpinska, E., et al. Chemical Abstracts 98:88987j.
"Synthesis of Optically Active 2-(N-Benzyl-N-methylamino)ethyl Methyl 2,6-Dimethyl-4-(m-nitrophenyl)-1,4-dihydropyridine-3-5-dicarboxylate (Nicardipine/)" by Tadao Shibanuma et al., *Chem. Pharm. Bull.*, 28, pt. 2809–2812 (1980).

"Derivatives of 1,3-Dimethyl-2-Azafluorene (1,3-Dimethyl-9-Indeno [2,1-c] Pyridine). H. Herbert Fox el al., Contribution No. 235 from the Research Laboratories of Hoffman-LaRoche Inc., p. 1259–1270 (1951).
E. Knoevenagle: Ueber den Chemismus der condensirenden Wirkung des Ammoniaks und organischer Amine bei Reactionen zwischen Aldehyden und Acetessigester Ber., 31, 738–748, (1899).
Houben-Weyl, "Methode der Organischen Chemie", vol. E5, Carbonsauren und Carbonsaure-Derivate, 1985, pp. 659–691, G. Thieme Verlag, Stuttgart.
Houben-Weyl, "Methode der Organischen Chemie", vol. III, Sauerstoffverbindungen III, 1952, pp. 516–522, 547–549, G. Thieme Verlag, Stuttgart.
Survey of Organic Syntheses, vol. 2, 1977, pp. 715–718, Buehler and Pearson, John Wiley & Sons.

Primary Examiner—Alan L. Rotman
Assistant Examiner—Dale A. Bjorkman
Attorney, Agent, or Firm—Cushman, Darby & Cushman

[57] ABSTRACT

Unsymmetrical 1,4-dihydropyridine-3,5-dicarboxylic acid diesters represented by the general formula

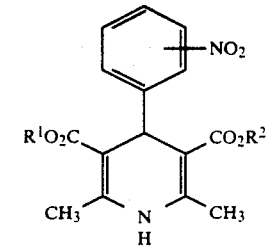

wherein $R^1$ and $R^2$ are different and represent each a nitratoalkyl having 2 or 3 carbon atoms, are prepared from the corresponding acid monoester in the presence of an organic acid anhydride activating agent. These compounds are useful as therapeutic agents for cardiovascular disorders.

3 Claims, No Drawings

METHOD FOR PREPARING UNSYMMETRICAL 1,4-DIHYDROPYRIDINE-3,5-DICARBOXYLIC ACID DIESTERS

BACKGROUND OF THE INVENTION

The present invention relates to a method for preparing 1,4-dihydropyridine-3,5-dicarboxylic acid diesters, and more particularly, it relates to unsymmetrical 1,4-dihydropyridine 3,5-dicarboxylic acid di(nitratoalkyl) esters useful as therapeutic agents for cardiovascular disorders.

In the past, 1,4-dihydropyridine-3,5-dicarboxylic acid di(nitratoalkyl) esters are prepared as shown in the following reaction schemes (U.S. Pat. No. 4,472,411).

Reaction Scheme 1

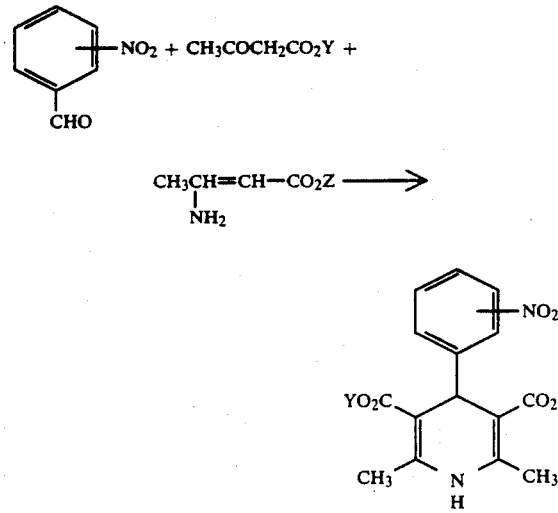

Reaction Scheme 2

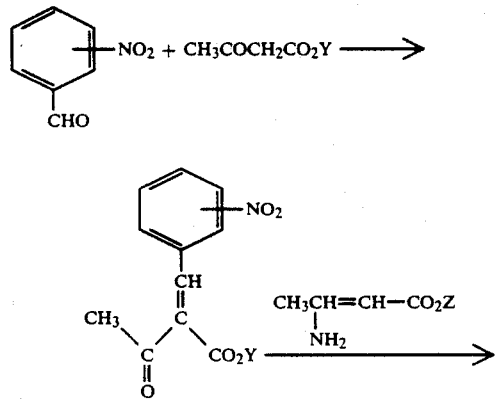

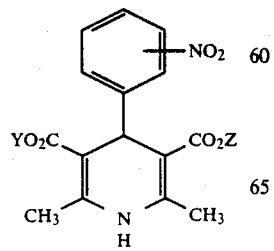

wherein Y and Z are each a nitratoalkyl group having 2 or 3 carbon atoms.

However, when Y and Z are different, these methods results in the formation of two by-products of symmetrical 1,4-dihydropyridine-3,5-dicarboxylic acid di(nitratoalkyl) esters represented by the following general formulae

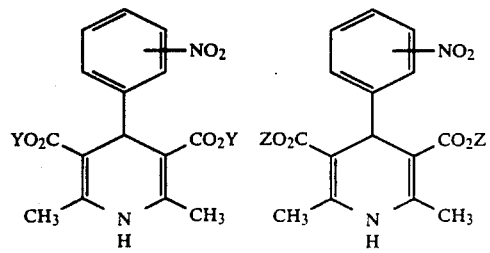

wherein Y and Z are as defined above. Although the formation of these by-products is in a small amount, since they are very similar in the physical properties to the objective compound of the unsymmetrical 1,4-dihydropyridine derivative, these methods require complicate purification procedure in order to give the objective compound in high purity. Accordingly, these methods are disadvantageous industrially.

On the other hand, there are known the methods for preparing some unsymmetrical 1,4-dihydropyridine-3,5-dicarboxylic acid diesters which comprises the esterification of the corresponding 3,5-dicarboxylic acid monoester with dialkylaminoethyl chloride (Reaction Scheme 3, U.S. Pat. No. 3,996,234), and which comprises the reaction of the corresponding 3,5-dicarboxylic acid monoester with phosphorus pentachloride, followed by the esterification of the resulting acid chloride with dialkylaminoethyl alcohol [Reaction Scheme 4; Chem. Pharm. Bull., 28(9), 2809 (1980)]. However, these methods can not be said to be advantageous industrially since the former method can only be applied to the compound having the substituent at the nitrogen atom of the dihydropyridine ring, and the yield of the latter method is low.

Reaction Scheme 3

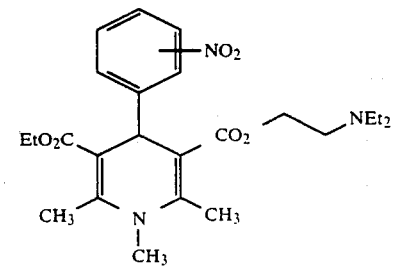

Reaction Scheme 4

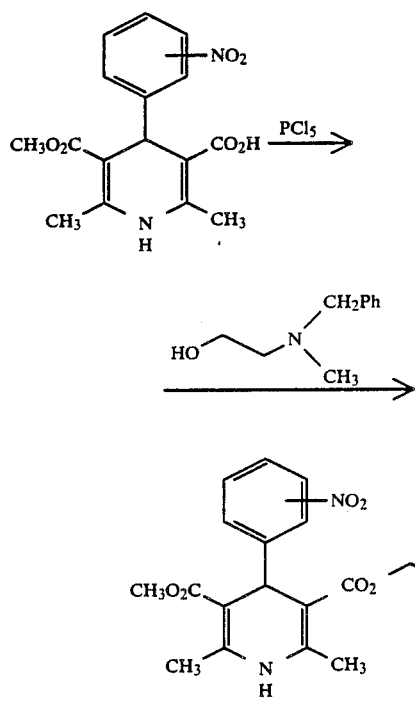

As a result of the earnest studies to resolve the drawbacks of the prior art methods, the present inventors have succeeded in preparing unsymmetrical 1,4-dihydropyridine-3,5-dicarboxylic acid diesters from 1,4-dihydroxypyridine-3,5-dicarboxylic acid monoesters in extremely high purity, and completed the present invention.

SUMMARY OF THE INVENTION

The present invention relates to a method for preparing an unsymmetrical 1,4-dihydropyridine-3,5-dicarboxylic acid diesters represented by the general formula

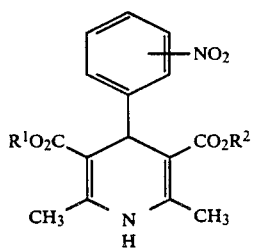

(I)

wherein $R^1$ and $R^2$ are different and represent each a nitratoalkyl group having 2 or 3 carbon atoms, which comprises reacting a 1,4-dihydropyridine-3,5-dicarboxylic acid monoester represented by the general formula

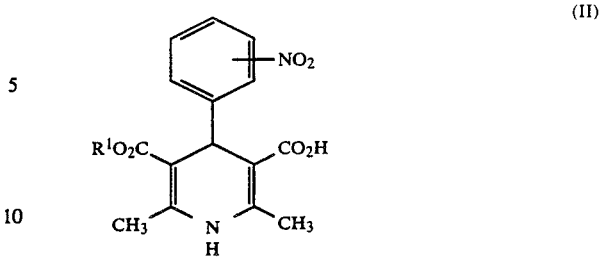

(II)

wherein $R^1$ is as defined above, with an activating reagent of the carboxylic acid, and reacting the resulting reactive derivative of the compound of formula II with an alcohol represented by the general formula $$R^2OH \quad (III)$$

wherein $R^2$ is as defined above.

DETAILED DESCRIPTION OF THE INVENTION

As used herein, "nitratoalkyl" for $R^1$ and $R^2$ means a 2-nitratoethyl, a 3-nitratopropyl, a 2-nitratopropyl, and 1-nitrato-2-propyl groups, and $R^1$ and $R^2$ are not the same.

The nitro group on the phenyl ring may occur at the 2- or 3-position.

The reaction of the compound of formula II with the activating reagent of the carboxylic acid is carried out in an inert solvent, water or a mixture of the inert solvent and water at the temperature from $-10°$ to $100°$ C., preferably $0°$ to $40°$ C.

As the activating reagents of the carboxylic acid, there are used those used conveniently in the art in order to obtain the reactive derivatives of the carboxylic acid (e.g., mixed acid anhydrides, activated esters and the like). Examples of these reagents are organic acid anhydrides (e.g., formic acetic anhydride, acetic benzoic anhydride, acetic anhydride, propionic anhydride, butyric anhydride, trifluoroacetic anhydride, benzoic anhydride and the like), acyl halides (e.g., acetyl chloride, propionyl chloride, valeryl chloride, benzoyl chloride, nicotinyl chloride, acetyl bromide, valeryl bromide and the like), halogenocarbonates (e.g., ethyl chlorocarbonate, propyl chlorocarbonate and the like), carbonate anhydrides (e.g., di-tert-butyldicarbonate and the like), 2-chloro-1-methylpyridinium iodide, 2,2'-dipyridyldisulfide, N-ethoxycarbonyl-2-ethoxy-1,2-dihydroquinoline and the like. The amount of the these reagents is at least an equivalent, preferably 1–4 equivalents to the compound of formula II.

This reaction may be carried out in the presence or absence of the catalyst. As the catalysts used, there are inorganic base (e.g., sodium hydroxide, potassium hydroxide, sodium carbonate, potassium carbonate, sodium hydride and the like), a mixture of the inorganic base described above and inorganic salt (e.g., calcium chloride, magnesium chloride and the like) and organic bases (e.g., triethylamine, pyridine and the like). The amount of these catalysts is at least an equivalent, preferably 1–3 equivalents relative to the compound of formula II. Furthermore, when the organic anhydride or acyl halide is used as the activating reagent, there also are used molecular sieves 3A, molecular sieves 4A, molecular sieves 5A, molecular sieves 13X, anhydrous sodium sulfate, anhydrous magnesium sulfate and the like. The amount of these catalysts is 0.05–5 parts, preferably 0.2–3 parts by weight relative to the compound of formula II. When 2,2'-dipyridyldisulfide is used as the reagent, there also may be used triphenylphosphin in the amount of at least an equivalent, preferably 1–2 equivalents relative to the compound of formula II. Preferably, this reaction can be carried out using acetic anhydride as the activating reagent in the presence of molecular sieves 3A, sodium hydroxide or a mixture of sodium hydroxide and calcium chloride.

Examples of the inert solvent used in the reaction are halogen type solvents such as dichloromethane, chloroform and the like; ether type solvents such as tetrahydrofuran, 1,2-dimethoxyethane, dioxane and the like; ester type solvents such as ethyl acetate and the like; and hydrocarbon type solvents such as benzene, toluene and the like.

The reactive derivative thus obtained, namely, the compound of formula II in which free carbonyl group is modified with an lower alkylcarbonyloxycarbonyl, substituted lower alkylcarbonyloxycarbonyl, phenylcarbonyloxycarbonyl, pyridylcarbonyloxycarbonyl, lower alkoxycarbonyloxycarbonyl, iodide 1-methylpyridinio-2-oxycarbonyl, S-2-pyridylthiocarbonyl, N-ethoxycarbonyl-1,2-dihydroxyquinoline-2-oxycarbonyl group or the like, can be used as such in the next step without isolation.

The reaction of the reactive derivative with the compound of formula III is carried out in the same inert solvent as those described above, water or a mixture of the solvent and water, at the temperature from −80° to 100° C., preferably −15° to 40° C. to give the compound of formula I.

This reaction may be carried out in the presence or absence of a catalyst. As the catalysts, there are used inorganic acids (e.g., hydrogen chloride, hydrogen bromide, sulfuric acid and the like), organic acids (e.g., p-toluenesulfonic acid, comphor-sulfonic acid and the like) and acyl halides (e.g., acetyl chloride, benzoyl chloride and the like), preferably acetyl chloride. The amount of these catalysts is 0.001–0.1 equivalent, preferably 0.01–0.1 equivalent relative to the compound of formula II used in the previous step. Furthermore, when used the activating reagent other than the organic anhydride or the acyl halide in the previous step, there may also be used inorganic bases (e.g., sodium hydride and the like) and organic bases (e.g., triethylamine and the like) in amounts of 0.1–2 equivalents, preferably 0.1–1 equivalent relative to the compound of formula II.

The compound of formula I thus obtained can be purified by the known techniques such as recrystallization or column chromatography.

The compound of formula II may be prepared, for example, by the following method: benzaldehyde of formula IV, acetoacetate of formula V and 3-aminocrotonate of formula VI

  NO₂  CH₃COCH₂CO₂R'  CH₃CH=CHCO₂R''
                                                  |
                                                  NH₂
CHO (IV)            (V)              (VI)

wherein one of R' and R" is R¹ and the other is —CH₂CH₂CN, are reacted in an organic solvent, water or a mixture of the organic solvent and water with heating according to the known method per se [J. Org. Chem., vol. 16, 1259(1951)] to give a compound represented by the general formula

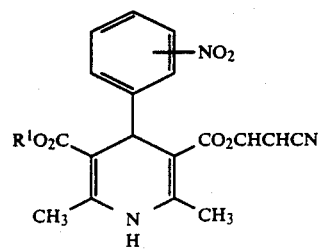

(VII)

wherein R¹ is as defined above.

In this reaction, there may be added a secondary amine, or an inorganic or organic acid salt thereof. Examples of the secondary amine are dimethylamine, diethylamine, diisopropylamine, pyrrolidine, piperidine, piperazine, N-methylpiperazine, morpholine and the like. Examples of the inorganic acid salt of the amine are the salts of hydrochloric acid, sulfuric acid, nitric acid, hydrobromic acid, phosphoric acid and the like, and examples of the organic acid salt of the amine are the salts of formic acid, acetic acid, trifluoroacetic acid, propionic acid, oxalic acid, benzoic acid, p-chlorobenzoic acid, o-chlorobenzoic acid, p-bromobenzoic acid, o-bromobenzoic acid, p-nitrobenzoic acid, 2,4-dinitrobenzoic acid, p-toluene-sulfonic acid and the like.

Examples of the organic solvent used are methanol, ethanol, isopropyl alcohol, dioxane, tetrahydrofuran, benzene, toluene and the like. The reaction temperature is preferably the boiling point of the solvent used, and the temperatures from 70° to 100° C. are suitable.

Alternatively, the compound of formula IV is reacted with the compound of formula V in an organic solvent in the presence of a basic catalyst or the same secondary amine as described above, the same inorganic or organic acid salt thereof as described above, at 0° to 105° C. to give a benzylidene derivative represented by the following general formula

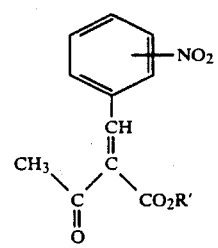

(VIII)

wherein R' is as defined above, and then this compound and the compound of formula VI are heated in an organic solvent or without solvent at the temperature from 50° to 100° C. to give the compound of formula VII [Ber., vol. 31, 743(1899)].

Examples of the organic solvent used in the first and second steps are benzene, toluene, xylene, ethanol, isopropyl alcohol, dioxane, tetrahydrofuran and the like.

Examples of the basic catalyst used are alkalis such as sodium hydroxide, potassium hydroxide, sodium ethoxide and the like.

Subsequently, the compound of formula VII is hydrolyzed with an alkali in a mixture of water and an organic solvent, and the reaction mixture is neutralized with an organic acid, the inorganic salt thereof, an inorganic acid, the inorganic salt thereof or a mixture consisting of 2 or more of the above to give the compound of formula II.

Examples of the organic solvent used are alcohol type solvents such as methanol, ethanol, isopropyl alcohol and the like, ether type solvents such as tetrahydrofuran, 1,2-dimethoxyethane and the like, acetone and the like.

Examples of the alkali used are sodium hydroxide, potassium hydroxide, calcium hydroxide, sodium carbonate, potassium carbonate, calcium carbonate, sodium bicarbonate and the like.

Examples of the organic acid used for neutralization are acetic acid, trifluoroacetic acid, oxalic acid, p-toluenesulfonic acid, benzoic acid and the like; examples of the inorganic salt thereof are sodium hydrogen oxalate, potassium hydrogen oxalate, sodium hydrogen succinate, potassium hydrogen succinate, sodium hydrogen phthalate, potassium hydrogen phthalate and the like; examples of the inorganic acid are hydrogen chloride, hydrobromic acid, sulfuric acid, phosphoric acid and the like; and examples of the inorganic salt thereof are sodium bisulfate, sodium dihydrogen phosphate and the like.

The present invention makes it possible to produce unsymmetrical 1,4-dihydropyridine-3,5-dicarboxylic acid diesters useful as therapeutic agents for cardiovascular disorders, in high yield and in high purity, therefore it is very valuable industrially.

The present invention is concretely illustrated below by Referential Examples and Examples.

REFERENTIAL EXAMPLE 1

10.3 g of 3-nitratopropyl acetoacetate, 7.7 g of 2-cyanoethyl 3-aminocrotonate and 7.6 g of 3-nitrobenzaldehyde in 76 ml of isopropyl alcohol were heated at reflux for 6.5 hours, and cooled on ice. The crystals which precipitated were collected by filtration, dried, applied to a silica gel column chromatography (eluent: dichloromethane) and recrystallized from ethanol to give 16.4 g of 2,6-dimethyl-4-(3-nitrophenyl)1,4-dihydropyridine-3,5-dicarboxylic acid 3-(2-cyanoethyl) ester 5-(3-nitratopropyl) ester.

m.p. 140°-141° C.

REFERENTIAL EXAMPLE 2

20.5 g of 2-nitratopropyl acetoacetate, 15.1 g of 3-nitrobenzaldehyde and 1.5 g of piperidine acetate in 74 ml of benzene were heated at reflux under azeotropic dehydration conditions for 2 hours. The reaction solution was washed, in turn, with 25 ml of water, 25 ml of an aqueous 1N sodium bisulfite solution and 25 ml of water and dried over anhydrous sodium sulfate, and the benzene was evaporated under reduced pressure. To the residue thus obtained was added 15.4 g of 2-cyanoethyl 3-aminocrotonate, and the mixture was taken up in 44 ml of isopropyl alcohol, heated at reflux for 3 hours and cooled on ice. The crystals which precipitated were collected by filtration, dried, applied to a silica gel column chromatography [eluent: a mixture of hexane and ethyl acetate (1:1)] and recrystallized from isopropyl alcohol to give 31.2 g of 2,6-dimethyl-4-(3-nitrophenyl)-1,4-dihydropyridine-3,5-dicarboxylic acid 3-(2-cyanoethyl) ester 5-(2-nitratopropyl) ester.

m.p. 139°-140.5° C.

REFERENTIAL EXAMPLE 3

20.5 g of 1-nitrato-2-propyl acetoacetate, 15.4 g of 2-cyanoethyl 3-aminocrotonate and 15.1 g of 3-nitrobenzaldehyde in 76 ml of isopropyl alcohol were heated at reflux for 6 hours. The mixture was treated in a manner similar to that of Referential Example 1, and the crystals thus obtained were applied to a silica gel column chromatography [eluent: a mixture of hexane and ethyl acetate (5:4)], and recrystallized from a mixture of dichloromethane and diethyl ether to give 31.3 g of 2,6-dimethyl-4-(3-nitrophenyl)-1,4-dihydropyridine-3,5-dicarboxylic acid 3-(2-cyanoethyl) ester 5-(1-nitrato-2-propyl) ester.

m.p. 138.5°-139.5° C.

REFERENTIAL EXAMPLE 4

9.7 g of 2-nitratoethyl acetoacetate, 7.7 g of 2-cyanoethyl 3-aminocrotonate and 7.6 g of 3-nitrobenzaldehyde in 76 ml of ethanol were heated at reflux for 7 hours. The mixture was treated in a manner similar to that of Referential Example 1, and the crystals thus obtained were applied to a silica gel column chromatography [eluent: a mixture of hexane and acetone (5:3)] and recrystallized from isopropyl alcohol to give 14.5 g of 2,6-dimethyl-4-(3-nitrophenyl)-1,4-dihydropyridine-3,5-dicarboxylic acid 3-(2-cyanoethyl) ester 5-(2-nitratoethyl) ester.

m.p. 131°-132.5° C.

REFERENTIAL EXAMPLE 5

10.2 g of 3-nitratopropyl 3-aminocrotonate, 7.8 g of 2-cyanoethyl acetoacetate and 7.7 g of 2-nitrobenzaldehyde in 77 ml of isopropyl alcohol were heated at reflux for 8 hours, and the isopropyl alcohol was evaporated under reduced pressure. The residue was applied to a silica gel column chromatography (eluent: dichloromethane) and recrystallized from a mixture of dichloromethane and diethyl ether to give 16.2 g of 2,6-dimethyl-4-(2-nitrophenyl)-1,4-dihydropyridine-3,5-dicarboxylic acid 3-(2-cyanoethyl) ester 5-(3-nitratopropyl) ester.

m.p. 132°-134° C.

REFERENTIAL EXAMPLE 6

9.7 g of 2-nitratoethyl acetoacetate, 7.6 g of 2-nitrobenzaldehyde and 0.2 g of piperidine in 40 ml of benzene were heated at reflux under azeotropic dehydration conditions for 3 hours. The mixture was treated in a manner similar to that of Referential Example 1, there was obtained the residue, to which was added 7.7 g of 2-cyanoethyl 3-aminocrotonate. The mixture was taken up in 40 ml of isopropyl alcohol and heated at reflux for 3 hours. The isopropyl alcohol was evaporated under reduced pressure, and the residue was applied to a silica gel column chromatography (eluent: dichromomethane) and recrystallized from a mixture of dichromethane and diethyl ether to give 14.3 g of 2,6-dimethyl-4-(2-nitrophenyl)-1,4-dihydropyridine-3,5-dicarboxylic acid 3-(2-cyanoethyl) ester 5-(2-nitratoethyl) ester.

m.p. 135°-136.5° C.

REFERENTIAL EXAMPLE 7

To 2.4 l of isopropyl alcohol were added 410 g of 3-nitratopropyl acetoacetate and 308 g of m-nitrobenzaldehyde, and then 14.5 g of piperidine acetate was added at 30° C. with stirring. The mixture was stirred for 24 hours, and the supernatant isopropyl alcohol layer was removed. To the residue were added in turn 3 l of isopropyl alcohol and 302 g of 2-cyanoethyl 3-aminocrotonate, and the mixture was heated at reflux for 8 hours and allowed to stand overnight at room temperature. The crystals which formed were collected by filtration and recrystallized from ethanol to give 804 g of 2,6-dimethyl-4-(3-nitrophenyl)-1,4-dihydropyridine-3,5-dicarboxylic acid 3-(2-cyanoethyl) ester 5-(3-nitratopropyl) ester.

m.p. 140°–141° C.

REFERENTIAL EXAMPLE 8

In 75 ml of acetone was dissolved 23.7 g of 2,6-dimethyl-4-(3-nitrophenyl)-1,4-dihydropyridine-3,5-dicarboxylic acid 3-(2-cyanoethyl) ester-5-(3-nitratopropyl) ester at 30° C., and 150 ml of an aqueous 1N-sodium hydroxide solution was added. The mixture was stirred at 30°–35° C. for 1.5 hours, and 150 ml of water was added. The mixture was washed 3 times with 25 ml of dichloromethane, and the aqueous layer was cooled on ice-water and neutralized with 1N-hydrochloric acid. The crystals which precipitated was collected by filtration, washed with 150 ml of water, dried and recrystallized from acetone to give 16.8 g of 2,6-dimethyl-4-(3-nitrophenyl)-1,4-dihydropyridine-3,5dicarboxylic acid 3-(3-nitratopropyl) ester.

m.p. 184°–185° C. (decomposition).

Following the procedure similar to that of the above, there were obtained the following compounds.

2,6-dimethyl-4-(3-nitrophenyl)-1,4-dihydropyridine-3,5-dicarboxylic acid 3-(2-nitratopropyl) ester.
  alkali used: sodium hydroxide.
  m.p. 173°–174° C. (decomposition).

2,6-dimethyl-4-(3-nitrophenyl)-1,4-dihydropyridine-3,5-dicarboxylic acid 3-(1-nitrato-2-propyl) ester.
  alkali used: sodium hydroxide.
  m.p. 178°–179° C. (decomposition).

2,6-dimethyl-4-(3-nitrophenyl)-1,4-dihydropyridine-3,5-dicarboxylic acid 3-(2-nitratoethyl) ester.
  alkali used: potassium hydroxide.
  m.p. 197°–198° C. (decomposition).

2,6-dimethyl-4-(2-nitrophenyl)-1,4-dihydropyridine-3,5-dicarboxylic acid 3-(3-nitratopropyl) ester.
  alkali used: potassium hydroxide.
  m.p. 179°–180° C. (decomposition).

2,6-dimethyl-4-(2-nitrophenyl)-1,4-dihydropyridine-3,5-dicarboxylic acid 3-(2-nitratoethyl) ester.
  alkali used: sodium hydroxide.
  m.p. 173°–174° C. (decomposition).

EXAMPLE 1

To a suspension of 10 g of 2,6-dimethyl-4-(3-nitrophenyl)-1,4-dihydropyridine-3,5-dicarboxylic acid 3-(3-nitratopropyl) ester in 50 ml of tetrahydrofuran were added dropwise, in turn, 2.7 g of triethylamine and 2.8 g of ethyl chlorocarbonate with ice-cooling, and the mixture was stirred for 2 hours. To this was added 3.1 g of 1,2-propanediol 1-nitrate, and the mixture was allowed to stand overnight with ice-cooling, poured into ice-water and extracted with dichloromethane. The dichloromethane layer was washed, in turn, with water, dilute hydrochloric acid, a saturated aqueous sodium bicarbonate solution and a saturated aqueous sodium chloride solution, and dried over anhydrous sodium sulfate. The solvent was evaporated, and the residue was recrystallized from diethyl ether to give 8.1 g of 2,6-dimethyl-4-(3-nitrophenyl)-1,4-dihydropyridine-3,5-dicarboxylic acid 3-(1-nitrato-2-propyl) ester 5-(3-nitratopropyl) ester.

m.p. 101°–103° C.

EXAMPLE 2

To a suspension of 10 g of 2,6-dimethyl-4-(3-nitrophenyl)-1,4-dihydropyridine-3,5-dicarboxylic acid 3-(3-nitratopropyl) ester in 50 ml of dichloromethane was added 3.7 g of acetyl chloride with ice-cooling, and the mixture was stirred for 30 minutes. To this was added 3.4 g of 1,2-propanediol 2-nitrate, and the mixture was stirred with ice-cooling for 4 hours, poured into ice-water, and then treated in a manner similar to that of Example 1. The residue thus obtained was recrystallized from ethanol to give 7.1 g of 2,6-dimethyl-4-(3-nitrophenyl)-1,4-dihydropyridine-3,5-dicarboxylic acid 3-(2-nitratopropyl) ester 5-(3-nitratopropyl) ester.

m.p. 87°–89° C.

EXAMPLE 3

2.04 g of 2,6-dimethyl-4-(3-nitrophenyl)-1,4-dihydropyridine-3,5-dicarboxylic acid 3-(2-nitratoethyl) ester and 1.22 g of triethylamine in 10 ml of tetrahydrofuran were stirred under a nitrogen atmosphere for 20 minutes, a solution of 1.54 g of 2-chloro-1-methylpyridinium iodide in 40 ml of acetonitrile was added dropwise with stirring, and the mixture was stirred at room temperature for an hour. To this was added 0.7 g of 1,2-propanediol 1-nitrate, and the mixture was allowed to stand overnight at room temperature. The reaction mixture was poured into ice water and treated in a manner similar to that of Example 1. The residue thus obtained was applied to a silica gel column chromatograpy (eluent: dichloromethane) and recrystallized from a mixture of diethyl ether and petroleum ether to give 1.0 g of 2,6-dimethyl-4-(3-nitrophenyl)-1,4-dihydropyridine-3,5-dicarboxylic acid 3-(2-nitratoethyl) ester 5-(1-nitrato-2-propyl) ester.

m.p. 93°–95° C.

EXAMPLE 4

2.1 g of 2,6-dimethyl-4-(2-nitrophenyl)-1,4-dihydropyridine-3,5-dicarboxylic acid 3-(3-nitratopropyl) ester and 1.24 g of 2,2'-dipyridyldisulfide were suspended in 10 ml of tetrahydrofuran under a nitrogen atmosphere, a solution of 1.46 g of triphenylphosphine in 10 ml of tetrahydrofuran was added dropwise with stirring at room temperature, and the mixture was stirred for 2 hours. The reaction solution was cooled on ice, a solution of 0.7 g of sodium 2-nitratoethoxide, previously prepared from sodium hydride and 2-nitratoethanol, in 5 ml of tetrahydrofuran was added dropwise. The mixture was stirred at room temperature for 5 hours, poured into ice-water and treated in a manner similar to that of Example 1. The residue thus obtained was applied to a silica gel column chromatography (eluent: dichloromethane) and recrystallized from a mixture of diethyl ether and petroleum ether to give 1.1 g of 2,6-dimethyl-4-(2-nitrophenyl)-1,4-dihydropyridine- 3,5-dicarboxylic acid 3-(2-nitratoethyl) ester 5-(3-nitratopropyl) ester.

m.p. 120.5°–121.5° C.

EXAMPLE 5

To a suspension of 4.21 g of 2,6-dimethyl-4-(3-nitrophenyl)-1,4-dihydropyridine-3,5-dicarboxylic acid 3-(3-nitratopropyl) ester in 50 ml of tetrahydrofuran were added, in turn, 2.36 g of N-ethoxycarbonyl-2-ethoxy-1,2-dihydroquinoline and 1.2 g of 1,2-propanediol 2-nitrate, and the mixture was stirred at room temperature for 7 hours. After completion of the reaction, the reaction mixture was extracted with dichloroethane, and the extract was washed, in turn, with 5% hydrochloric acid and water. The solvent was evaporated, and the residue was recrystallized from ethanol to give 2.6 g of 2,6-dimethyl-4-(3-nitrophenyl)-1,4-dihydropyridine-3,5-dicarboxylic acid 3-(2-nitratopropyl) ester 5-(3-nitratopropyl) ester.

m.p. 87°–89° C.

EXAMPLE 6

In 1.1 l of an aqueous 1N sodium hydroxide solution was dissolved 421.31 g of 2,6-dimethyl-4-(3-nitrophenyl)-1,4-dihydropyridine-3,5-dicarboxylic acid 3-(3-nitratopropyl) ester, and the solution was cooled throughly on ice-water. To the solution was added dropwise 1.1 l of a cold saturated aqueous sodium chloride solution with stirring. The aqueous layer was removed by decantation, and the residue was washed twice with 1 l of a cooled saturated aqueous sodium chloride solution, and suspended in 1 l of dichloromethane. To the suspension was added dropwise 204.2 g of acetic anhydride with ice-cooling, and the mixture was stirred for 30 minutes. The dichloromethane layer was collected and dried over anhydrous sodium sulfate, and the anhydrous sodium sulfate was removed by filtration. To the dichloromethane layer were added, in turn, 145.3 g of 1,2-propanediol 2-nitrate and 18 g of a 5% hydrogen chloride dichloromethane solution with water cooling, and the mixture was stirred for 2 hours. The reaction solution was washed, in turn, each twice with 400 ml of a 5% aqueous sodium carbonate solution and 400 ml of a saturated aqueous sodium chloride solution, and dried over anhydrous sodium sulfate. The solvent was evaporated, and the residue was recrystallized from ethanol to give 428 g of 2,6-dimethyl-4-(3-nitrophenyl)-1,4-dihydropyridine-3,5-dicarboxylic acid 3-(2-nitratopropyl) ester 5-(3-nitratopropyl) ester.

m.p. 87°–89° C.

EXAMPLE 7

In 1.1 l of an aqueous 1N sodium hydroxide solution was dissolved 421.31 g of 2,6-dimethyl-4-(3-nitrophenyl)-1,4-dihydropyridine-3,5-dicarboxylic acid 3-(3-nitratopropyl) ester, and 2 l of dichloromethane was added. To the mixture was added 66.6 g of anhydrous calcium chloride in 222 ml of water with stirring, and the mixture was stirred at room temperature for 30 minutes. The dichloromethane layer was collected and dried over anhydrous calcium chloride, and the anhydrous calcium chloride was removed. The dichloromethane solution was cooled on water, and 204.2 g of acetic anhydride was added. The mixture was stirred with ice cooling for 30 minutes, and the precipitate was removed. To the dichloromethane solution was added, in turn, 145.3 g of 1,2-propanediol 2-nitrate and 3.93 g of acetyl chloride with water cooling, the mixture was stirred for 2 hours. The reaction solution was washed, in turn, each twice with 400 ml of a 5% aqueous sodium carbonate solution and 400 ml of a saturated aqueous sodium chloride solution, and dried over anhydrous sodium sulfate. The solvent was evaporated, and the residue was recrystallized from ethanol to give 445 g of 2,6-dimethyl-4-(3-nitrophenyl)-1,4-dihydropyridine-3,5-dicarboxylic acid 3-(2-nitratopropyl) ester 5-(3-nitratopropyl) ester.

m.p. 87°–89° C.

EXAMPLE 8

210.7 g of 2,6-dimethyl-4-(3-nitrophenyl)-1,4-dihydropyridine-3,5-dicarboxylic acid 3-(3-nitratopropyl) ester was suspended in 1 ( of dichloromethane, and then 105 g of molecular seives 3A and 153 g of acetic anhydride were added in turn at room temperature. The mixture was stirred for 2 hours, and the molecular seives 3A was removed by filtration. To the dichloromethane solution cooled at 10° C. were added 72.7 g of cooled (10° C.) 1,2-propanediol 2-nitrate and 2 g of acetyl chloride with stirring. The mixture was stirred at 10° to 20° C. for 4 hours, and a solution of 175 g of sodium carbonate in 875 ml of water was added dropwise with ice cooling with stirring. After no more foam was formed, the dichloromethane layer was collected, washed, in turn, each twice with 200 ml of a 5% aqueous sodium carbonate solution and 200 ml of a saturated aqueous sodium chloride solution, and dried over anhydrous sodium sulfate. The solvent was evaporated, and the residue was recyrstallized from ethanol to give 239.8 g of 2,6-dimethyl-4-(3-nitrophenyl)-1,4-dihydropyridine-3,5-dicarboxylic acid 3-(2-nitratopropyl) ester 5-(3-nitratopropyl) ester.

m.p. 87°–89° C.

What is claimed is:

1. A method for preparing an unsymmetrical 1,4-dihydropyridine-3,5-dicarboxylic acid diester represented by the general formula

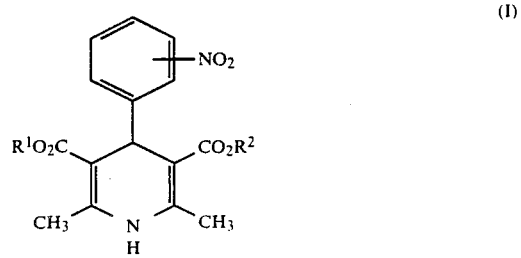

(I)

wherein $R^1$ and $R^2$ are different and represent each a nitratoalkyl group having 2 or 3 carbon atoms, which comprises reacting a 1,4-dihydropyridine-3,5-dicarboxylic acid monoester represented by the general formula

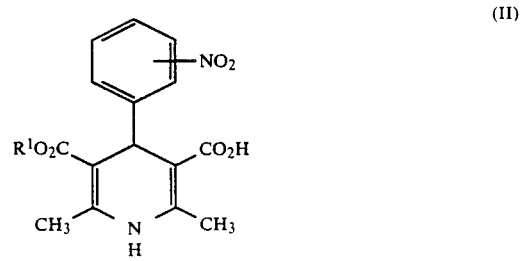

(II)

wherein $R^1$ is as defined above, with an activating reagent of the carboxylic acid which activating reagent is an organic acid anhydride in the pressure of a catalyst of an inorganic base, a mixture of the inorganic base and an inorganic salt, an organic base, molecular sieves 3A, molecular sieves 4A, molecular sieves 5A, molecular sieves 13X, anhydrous sodium sulfate or anhydrous magnesium sulfate, and reacting the resulting reactive derivative of the compound of formula II with an alcohol represented by the general formula $$R^2OH \quad \quad (III)$$

wherein $R^2$ is as defined above.

2. The method as claimed in claim 1, wherein the activating reagent is acetic anhydride in the pressure of molecular sieves 3A, sodium hydroxide or a mixture of sodium hydroxide and calcium chloride.

3. The method as claimed in claim 1, wherein the compound of formula I is 2,6-dimethyl-4-(3-nitrophenyl)-1,4-dihydropyridine-3,5-dicarboxylic acid 3-(2-nitratopropyl) ester 5-(3-nitratopropyl) ester.

* * * * *